(12) United States Patent
Falbe

(10) Patent No.: US 6,476,251 B2
(45) Date of Patent: Nov. 5, 2002

(54) PROCESS FOR PREPARING SPIROCYCLIC TETRONIC ACID DERIVATIVES

(75) Inventor: Volker Falbe, Wuppertal (DE)

(73) Assignees: Bayer Aktiengesellschaft, Leverkusen (DE); Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/804,273

(22) Filed: Mar. 12, 2001

(65) Prior Publication Data

US 2001/0039355 A1 Nov. 8, 2001

(30) Foreign Application Priority Data

Mar. 16, 2000 (DE) .......................... 100 12 825

(51) Int. Cl.[7] .......................... C07C 69/00; C07C 69/34
(52) U.S. Cl. .................. 560/129; 560/193; 560/194; 549/296; 549/297; 549/298
(58) Field of Search ................. 549/298, 296, 549/297; 560/194, 193, 129

(56) References Cited

U.S. PATENT DOCUMENTS

| | | | |
|---|---|---|---|
| 5,262,383 A | * 11/1993 | Fisher et al. | |
| 5,585,504 A | 12/1996 | Desmond et al. | ........... 549/323 |
| 5,610,122 A | * 3/1997 | Fisher et al. | |
| 5,719,310 A | * 2/1998 | Fischer et al. | |
| 5,830,825 A | * 11/1998 | Fischer et al. | |
| 5,994,274 A | * 11/1999 | Fischer et al. | |
| 6,110,872 A | * 8/2000 | Lieb et al. | |
| 6,140,358 A | * 10/2000 | Lieb et al. | |
| 6,288,102 B1 | * 9/2001 | Hagemann et al. | |

OTHER PUBLICATIONS

Priority date: PCT Publication Date.*

* cited by examiner

Primary Examiner—Alan L. Rotman
Assistant Examiner—Héctor M Reyes
(74) Attorney, Agent, or Firm—Joseph C. Gil; John E. Mrozinski, Jr.

(57) ABSTRACT

The present invention relates to a novel process for preparing compounds of the formula (I)

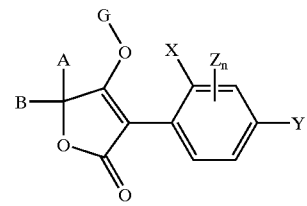

by reacting compounds of the formula (II)

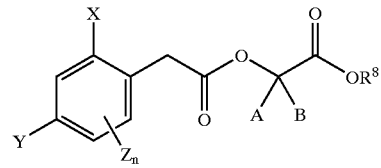

with a base and compounds of the formula (III)

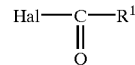

in which X, Y, Z, n, G, A, B, $R^1$, $R^8$ and Hal are each as defined above.

6 Claims, No Drawings

PROCESS FOR PREPARING SPIROCYCLIC TETRONIC ACID DERIVATIVES

The present invention relates to a novel process for preparing known spirocyclic tetronic acid derivatives.

The multi-step synthesis of spirocyclic tetronic acid derivatives is known (EP-A-528 156).

It has now been found that compounds of the formula (I)

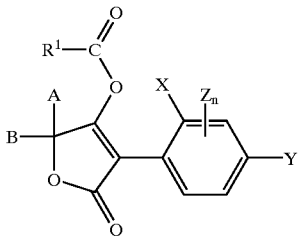

(I)

in which

X represents alkyl, halogen, alkoxy or halogenoalkyl,

Y represents hydrogen, alkyl, halogen, alkoxy or halogenoalkyl,

Z represents alkyl, halogen or alkoxy, n represents a number from 0 to 3, or the radicals X and Z together with the phenyl radical to which they are attached form the naphthalene radical of the formula

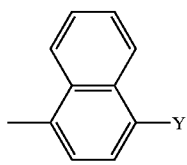

in which Y is as defined above,

A represents an in each case optionally substituted radical from the group consisting of alkyl, alkenyl, alkoxyalkyl, polyalkoxyalkyl and alkylthioalkyl, represents in each case saturated or unsaturated and optionally substituted cycloalkyl or heterocyclyl or represents in each case optionally halogen-, alkyl-, halogenoalkyl-, alkoxy-, halogenoalkoxy-, cyano- or nitro-substituted aryl, arylalkyl or hetaryl, B represents alkyl or alkoxyalkyl or A and B together with the carbon atom to which they are attached represent a saturated or unsaturated, optionally substituted carbocycle or heterocycle, $R^1$ represents in each case optionally halogen-substituted alkyl, alkenyl, alkoxy, alkenyloxy, alkoxyalkyl, alkylthioalkyl, polyalkoxyalkyl or optionally substituted cycloalkyl which may be interrupted by heteroatoms, represents optionally substituted phenyl or phenoxy, optionally substituted phenylalkyl or phenylalkyloxy, substituted hetaryl, substituted phenoxyalkyl or substituted hetaryloxyalkyl, and the stereo- and enantiomerically pure forms of compounds of the formula (I) are obtained when compounds of the formula (II)

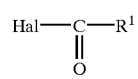

(II)

in which

X, Y, Z, n, A and B are each as defined above and $R^8$ represents alkyl are reacted with a base and compounds of the formula (III)

$$Hal-\underset{\underset{O}{\|}}{C}-R^1$$

(III)

in which $R^1$ is as defined above and

Hal represents halogen, in particular chlorine or bromine, if appropriate in the presence of a diluent.

Using the process according to the invention, it is surprisingly possible to prepare the abovementioned compounds in a simpler manner in a one-pot process, without isolation of the intermediates, in higher purity and with better yields.

In the general formulae (I), (II) and (III), the substituents

X preferably represents $C_1$–$C_6$-alkyl, halogen, $C_1$–$C_6$-alkoxy or $C_1$–$C_3$-halogenoalkyl, Y preferably represents hydrogen, $C_1$–$C_6$-alkyl, halogen, $C_1$–$C_6$-alkoxy or $C_1$–$C_3$-halogenoalkyl, Z preferably represents $C_1$–$C_6$-alkyl, halogen or $C_1$–$C_6$-alkoxy, n preferably represents a number from 0 to 3, or the radicals X and Z together with the phenyl radical to which they are attached form the naphthalene radical of the formula

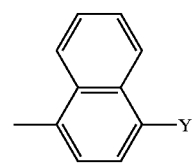

in which Y is defined as above,

A preferably represents in each case optionally halogen-substituted $C_1$–$C_{12}$-alkyl, $C_2$–$C_8$-alkenyl, $C_1$–$C_{10}$-alkoxy-$C_1$–$C_8$-alkyl, represents optionally halogen-, $C_1$–$C_6$-alkyl- or $C_1$–$C_6$-alkoxy-substituted $C_3$–$C_8$-cycloalkyl, in which optionally one or two not directly adjacent methylene groups are replaced by oxygen and/or sulphur or represents in each case optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl or phenyl-$C_1$–$C_6$-alkyl, B preferably represents $C_1$–$C_{12}$-alkyl or $C_1$–$C_8$-alkoxy-$C_1$–$C_6$-alkyl or A, B and the carbon atom to which they are attached preferably represent $C_5$–$C_{10}$-cycloalkyl or $C_5$–$C_{10}$-cycloalkenyl in which optionally one methylene group is replaced by oxygen or sulphur and which are optionally substituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl or A, B and the carbon to which they are attached preferably represent $C_5$–$C_8$-cycloalkyl or $C_5$–$C_8$-cycloalkenyl in which two carbon atoms are attached to one another by in each case optionally $C_1$–$C_6$-alkyl-, $C_1$–$C_6$-alkoxy- or halogen-substituted $C_3$–$C_6$-alkanediyl, $C_3$–$C_6$-alkenediyl or $C_4$–$C_6$-alkanedienediyl in which in each case optionally one methylene group is replaced by oxygen or sulphur, $R^8$ preferably represents $C_1$–$C_6$-alkyl, Hal preferably represents chlorine or bromine, $R^1$ preferably represents in each case optionally halogen-substituted $C_1$–$C_{20}$-alkyl, $C_1$–$C_{20}$-alkoxy, $C_2$–$C_{20}$-alkenyl, $C_3$–$C_{10}$-alkenyloxy, $C_1$–$C_8$-alkoxy-$C_1$–$C_8$-alkyl, $C_1$–$C_8$-alkylthio-$C_1$–$C_8$-alkyl, optionally $C_1$–$C_6$-alkyl-, $C_1$–$C_6$-alkoxy-, fluorine- or chlorine-substituted cycloalkyl having 3 to 8 ring atoms which may be interrupted by oxygen and/or sulphur atoms, preferably represents in each case optionally halogen-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl or phenoxy;

preferably represents in each case optionally halogen-, $C_1$–$C_6$-alkyl-, $C_1$–$C_6$-alkoxy-, $C_1$–$C_6$-halogenoalkyl-, $C_1$–$C_6$-halogenoalkoxy-substituted phenyl-$C_1$–$C_6$-alkyl or phenyl-$C_1$–$C_4$-alkyloxy, preferably represents optionally halogen- or $C_1$–$C_6$-alkyl-substituted hetaryl, preferably represents optionally halogen- or $C_1$–$C_6$-alkyl-substituted phenoxy-$C_1$–$C_6$-alkyl, preferably represents optionally halogen-, amino- or $C_1$–$C_6$-alkyl-substituted hetaryloxy-$C_1$–$C_6$-alkyl.

In the general formulae (I), (II) and (III), the substituents

X particularly preferably represents $C_1$–$C_4$-alkyl, fluorine, chlorine, bromine, $C_1$–$C_4$-alkoxy or $C_1$–$C_2$-halogenoalkyl, Y particularly preferably represents hydrogen, $C_1$–$C_4$-alkyl, fluorine, chlorine, bromine, $C_1$–$C_4$-alkoxy or $C_1$–$C_2$-halogenoalkyl, Z particularly preferably represents $C_1$–$C_4$-alkyl, fluorine, chlorine, bromine or $C_1$–$C_4$-alkoxy, n particularly preferably represents a number from 0 to 2, A, B and the carbon atom to which they are attached particularly preferably represent $C_5$–$C_8$-cycloalkyl in which in each case optionally one methylene group is replaced by oxygen or sulphur and which is optionally substituted by $C_1$–$C_6$-alkyl, $C_1$–$C_3$-halogenoalkyl, $C_1$–$C_6$-alkoxy, fluorine or chlorine, or A, B and the carbon atom to which they are attached particularly preferably represent $C_5$–$C_6$-cycloalkyl in which two carbon atoms are attached to one another by in each case optionally $C_1$–$C_4$-alkyl-, $C_1$–$C_4$-alkoxy-, fluorine-, chlorine- or bromine-substituted $C_3$–$C_5$-alkanediyl, $C_3$–$C_5$-alkenediyl, in which in each case optionally one methylene group is replaced by oxygen or sulphur, or attached to one another by butadienediyl, $R^8$ particularly preferably represents $C_1$–$C_4$-alkyl, Hal particularly preferably represents chlorine or bromine, $R^1$ particularly preferably represents in each case optionally fluorine- or chlorine-substituted $C_1$–$C_{16}$-alkyl, $C_1$–$C_{16}$-alkoxy, $C_3$–$C_6$-alkenyloxy, $C_2$–$C_{16}$-alkenyl, $C_1$–$C_6$-alkoxy-$C_1$–$C_4$-alkyl, $C_1$–$C_6$-alkylthio-$C_1$–$C_4$-alkyl, optionally methyl-, ethyl-, methoxy-, fluorine- or chlorine-substituted cycloalkyl having 3 to 7 ring atoms which may be interrupted by 1 or 2 oxygen and/or sulphur atoms, represents in each case optionally fluorine-, chlorine-, bromine-, nitro-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl, phenoxy or benzyloxy, represents optionally halogen- or $C_1$–$C_6$-alkyl-substituted hetaryl.

In the general formulae (I), (II) and (III), the substituents

X very particularly preferably represents methyl, ethyl, propyl, i-propyl, fluorine, chlorine, bromine, methoxy, ethoxy or trifluoromethyl, Y very particularly preferably represents hydrogen, methyl, ethyl, propyl, i-propyl, butyl, i-butyl, tert-butyl, fluorine, chlorine, bromine, methoxy, ethoxy or trifluoromethyl, Z very particularly preferably represents methyl, ethyl, i-propyl, butyl, i-butyl, tert-butyl, fluorine, chlorine, bromine, methoxy or ethoxy, n very particularly preferably represents the number 0 to 1, A, B and the carbon atom to which they are attached very particularly preferably represent $C_3$–$C_8$-cycloalkyl in which in each case optionally one methylene group is replaced by oxygen or sulphur and which is optionally substituted by methyl, ethyl, n-propyl, iso-propyl, trifluoromethyl, methoxy, ethoxy, n-propoxy, iso-propoxy, butoxy or iso-butoxy, $R^8$ very particularly preferably represents methyl, ethyl, propyl or iso-propyl, Hal very particularly preferably represents chlorine or bromine, $R^1$ very particularly preferably represents in each case optionally fluorine- or chlorine-substituted $C_1$–$C_{14}$-alkyl, $C_1$–$C_{10}$-alkoxy, $C_2$–$C_{14}$-alkenyl, $C_3$–$C_6$-alkenyloxy, $C_1$–$C_4$-alkoxy-$C_1$–$C_2$-alkyl, $C_1$–$C_4$-alkylthio-$C_1$–$C_2$-alkyl or cycloalkyl having 3 to 6 ring atoms which may be interrupted by 1or 2 oxygen and/or sulphur atoms, represents in each case optionally fluorine-, chlorine-, bromine-, methyl-, ethyl-, propyl-, i-propyl-, methoxy-, ethoxy-, trifluoromethyl-, trifluoromethoxy-, nitro-substituted phenyl, phenoxy or benzyloxy;

represents optionally chlorine-, methyl- or ethyl-substituted pyridyl.

A very particularly preferred compound of the formula (I) is the compound of the formula (Ia)

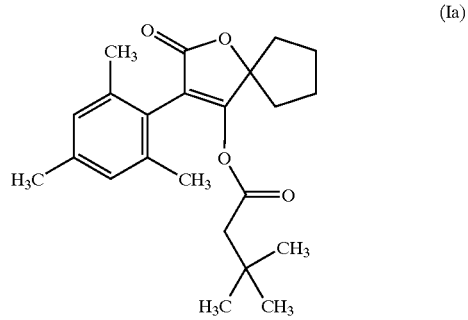

(Ia)

which is obtained by reacting the compound of the formula (IIa)

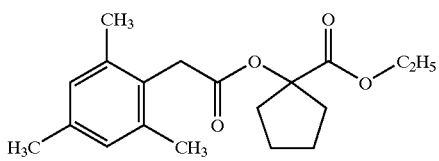

with NaOH and the compound of the formula (IIIa)

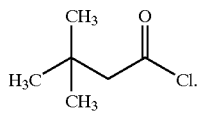

A further very particularly preferred compound of the formula (I) is the compound of the formula (Ib)

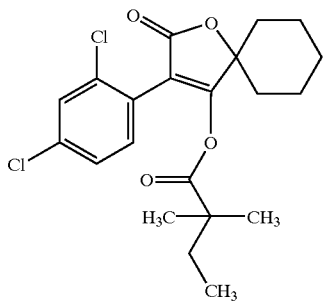

which is obtained by reacting the compound of the formula (IIb)

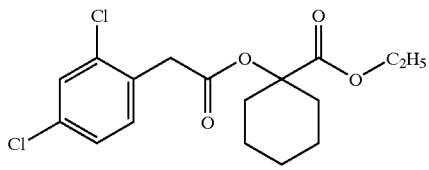

with NaOH and the compound of the formula (IIIb)

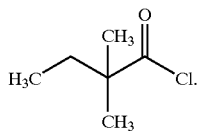

Suitable bases (deprotonating agents) for the ring-closure reaction are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (methyltrialkyl-($C_8$–$C_{10}$)-ammonium chloride) or TDA 1 (tris-(methoxyethoxyethyl)-amine). It is furthermore possible to use alkali metals such as sodium or potassium. Also suitable are alkali metal and alkaline earth metal amides and hydrides, such as sodium amide, sodium hydride and calcium hydride, and furthermore also alkali metal alkoxides, such as sodium methoxide, sodium ethoxide and potassium tert-butoxide, or else tertiary amines, such as diazabicyclooctane (DABCO), diazabicycloundecene (DBU), diazabicyclononene (DBN) and Hünig base.

Suitable diluents for the ring-closure reaction are all solvents which are inert to the base that is used. Preference is given to using hydrocarbons, such as benzine, benzene, toluene, xylene and tetraline, furthermore halogenated hydrocarbons, such as methyl chloride, chlorobenzene and o-dichlorobenzene, moreover ethers, such as diethyl ether, methyl tert-butyl ether, tert-amyl ether, tetrahydrofuran and dioxane, additionally strongly polar solvents, such as N,N-dimethylformamide, N,N-dimethylacetamide, N-methylpyrrolidone, dimethyl sulphoxide and sulpholane.

After the ring-closure reaction has taken place, the acid halide is added to the reaction solution.

To scavenge residual hydrogen chloride from the acid chloride preparation, it is possible to add small amounts of customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate.

In the process according to the invention, the reaction temperatures can be varied within a relatively wide range. In general, the process is carried out at temperatures between −20° C. and +200° C., preferably between 0° C. and 150° C.

The reaction is generally carried out under reduced pressure, preferably in a range of 50–500 mbar.

When carrying out the process according to the invention, the reaction components of the formulae (II) and (III) and the deprotonating bases are generally employed in approximately equimolar amounts. However, it is also possible to use a relatively large excess (up to 5 mol, preferably up to 2 mol) of one or the other component.

The starting materials of the formula (II) are known. Their preparation is described in EP-A-647 637. The carbonyl halides of the formula (III) are likewise known. They are commercially available or can be prepared by generally customary processes of organic chemistry.

The preparation of the compounds of the formula (I) is illustrated by the Preparation Examples below.

Preparation Examples

EXAMPLE 1

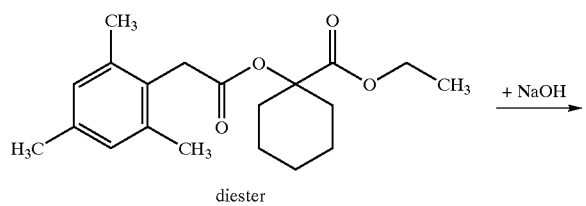

diester

-continued

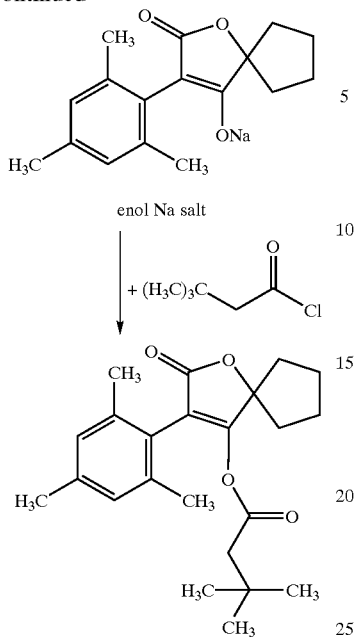

enol Na salt

In a flask, 1.1 mol of sodium hydroxide are initially charged in 500 ml of N,N-dimethylacetamide, the pressure is reduced to 200 mbar and the mixture is heated. A solution of 1 mol of diester in about 225 ml of N,N-dimethylacetamide is then metered in over a period of 4 h, and at the same time, distillate is removed at a rate of about 50 ml/h. The mixture is stirred for a further 2 h, while the distillate is still removed at a rate of about 50 ml/h. At 200 mbar, a further about 70 g of distillate are then removed. At the end, the amount of distillation bottom is 688.5 g.

The conversion into the enol Na salt is determined as follows:

At room temperature, 1/10 of the distillation bottom is added with stirring to 150 ml of 5% strength hydrochloric acid. The precipitated enol is filtered off, triturated with 100 ml of water, filtered again and dried under reduced pressure at 50° C. This gives 22.4 g of enol of a purity of 88.0% (72.4% of theory); another 1.5% (8.8% of theory) of enol are detected in the mother liquor (152.4 g), and another 0.43% (1.6% of theory) of enol are found in the wash water (101.5 g). The total yield of enol is thus 82.8% of theory.

137.7 g of the bottom, together with about 15 mol % of triethylamine (to scavenge residual HCl from the preparation of the acid chloride) are initially charged in a flask in 130 ml of methylcyclohexane. At from 25 to 30° C., 0.25 mol of 3,3-dimethylbutyryl chloride are metered in over a period of 2 h. The mixture is stirred at from 25 to 30° C. for 2 h. Without cooling, the reaction mixture is then metered into a solution of 8.4 g of sodium bicarbonate in 320 ml of water. The mixture is heated to 50° C. and stirred at this temperature for 1 h. The aqueous phase is removed, and 80 ml of water are then added. The mixture is stirred at 50° C. for 30 min, and the aqueous phase is removed. The organic phase is cooled to 35° C., admixed with seed crystals and stirred at 25° C. for 1 h. The organic phase is then slowly cooled to −10° C. and stirred at this temperature for 1 h.

Precipitated product is filtered and dried: 51.7 g (68.4% of theory, based on the diester employed).

EXAMPLE 2

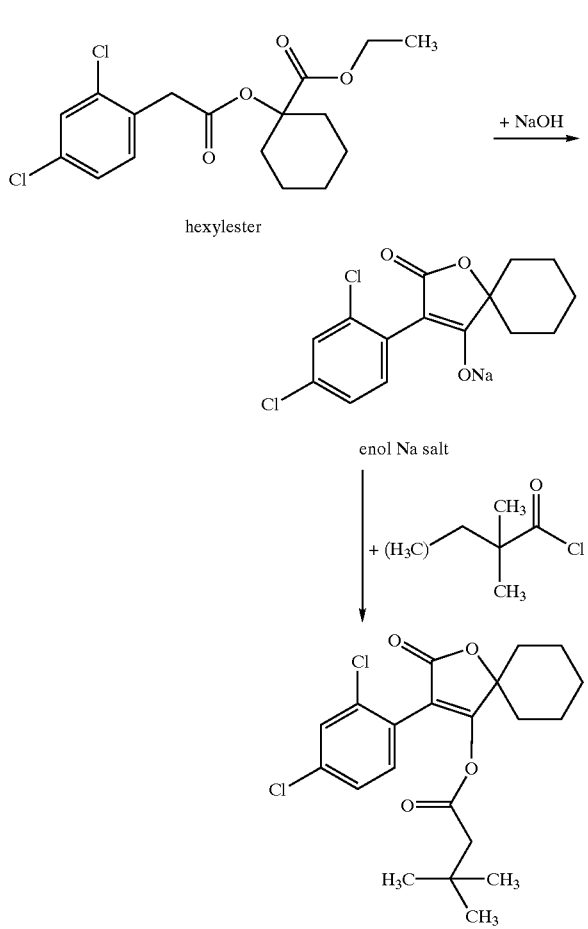

In a flask, 2.2 mol of sodium hydroxide are initially charged in 1000 ml of N,N-dimethylacetamide, the pressure is reduced to 200 mbar and the mixture is heated. A solution of 2 mol of hexyl ester in about 1150 ml of N,N-dimethylacetamide is then metered in over a period of 4 h, and at the same time, distillate is removed at a rate of about 200 g/h. The mixture is stirred for a further 2 h, while the distillate is still removed at a rate of about 200 g/h. At 200 mbar, a further about 120 g of distillate are then removed. At the end, the amount of distillation bottom is 1484 g.

The conversion into the enol Na salt is determined by two methods:

1. A sample of the bottom is examined by HPLC. The Na salt is determined as free enol. The enol content is found to be 40.0%; this corresponds to a yield of 94.8% of theory, based on the hexyl ester.
2. At room temperature, 1/20 of the distillation bottom is added with stirring to 150 ml of 5% strength hydrochloric acid. The precipitated enol is filtered off, triturated with 100 ml of water, filtered again and dried under reduced pressure at 50° C. This gives 32.4 g of enol of a purity of 94.4%; this corresponds to a yield of 97.6% of theory, based on the hexyl ester.

148 g of the bottom, together with about 15 mol % of triethylamine (to scavenge residual HCl from the preparation of the acid chloride) are initially charged in a flask in 130 ml of methylcyclohexane. At from 25 to 30° C., 0.25 mol of 2,2-dimethylbutyryl chloride are metered in over a period of 2 h. The mixture is stirred at from 25 to 30° C. for 2 h. Without cooling, the reaction mixture is then metered into a solution of 8.4 g of sodium bicarbonate in 320 ml of water. The mixture is heated to 50° C. and stirred at this temperature for 1 h. The aqueous phase is removed, and 80 ml of water are then added. The mixture is stirred at 50° C. for 30 min, and the aqueous phase is removed. The organic phase is cooled to 35° C., admixed with seed crystals and stirred at 25° C. for 1 h. The organic phase is then slowly cooled to −10° C. and stirred at this temperature for 1 h. Precipitated product is filtered and dried: 73.7 g (89.1% of theory, based on the hexyl ester employed).

What is claimed is:

1. A process for preparing a compound of the formula (I)

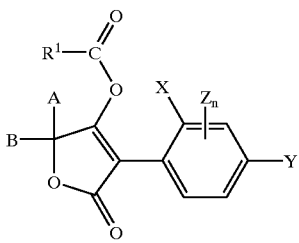

(I)

wherein

X represents alkyl, halogen, alkoxy or halogenoalkyl,

Y represents hydrogen, alkyl, halogen, alkoxy or halogenoalkyl,

Z represents alkyl, halogen or alkoxy, n represents a number from 0 to 3, or the radicals X and Z together with the phenyl radical to which they are attached form a naphthalene radical of the formula

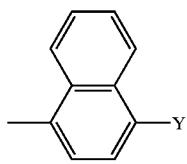

in which Y is as defined above,

A represents an optionally substituted radical selected from the group consisting of alkyl, alkenyl, alkoxyalkyl, polyalkoxyalkyl and alkylthioalkyl, represents saturated or unsaturated and optionally substituted cycloalkyl or heterocyclyl or represents optionally halogen-, alkyl-, halogenoalkyl-, alkoxy-, halogenoalkoxy-, cyano- or nitro-substituted aryl, arylalkyl or hetaryl, B represents alkyl or alkoxyalkyl or A and B together with the carbon atom to which they are attached represent a saturated or unsaturated, optionally substituted carbocycle or heterocycle, $R^1$ represents optionally halogen-substituted alkyl, alkoxy, alkenyl, alkenyloxy, alkoxyalkyl, alkylthioalkyl, polyalkoxyalkyl or optionally substituted cycloalkyl which may be interrupted by heteroatoms, represents optionally substituted phenyl or phenoxy, optionally substituted phenylalkyl or phenylalkyloxy, substituted hetaryl, substituted phenoxyalkyl or substituted hetaryloxyalkyl, said process comprising deprotonating with a base a compound of the formula (II)

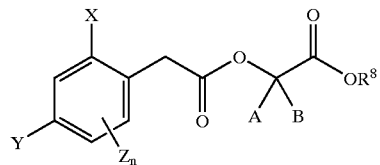

(II)

wherein

X, Y, Z, n, A and B are as defined above and $R^8$ represents alkyl;

reacting the deprotonated compound with a compound of the formula (III)

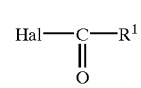

(III)

wherein $R^1$ is as defined above and

Hal represents halogen; and collecting the reaction product.

2. A process for preparing a compound of the formula (I)

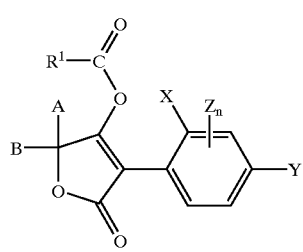

(I)

wherein

X represents $C_1$–$C_6$-alkyl, halogen, $C_1$–$C_6$-alkoxy or $C_1$–$C_3$-halogenoalkyl, Y represents hydrogen, $C_1$–$C_6$-alkyl, halogen, $C_1$–$C_6$-alkoxy or $C_1$–$C_3$-halogenoalkyl, Z represents $C_1$–$C_6$-alkyl, halogen or $C_1$–$C_6$-alkoxy, n represents a number from 0 to 3, or the radicals X and Z together with the phenyl radical to which they are attached form a naphthalene radical of the formula

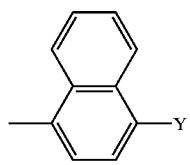

in which Y is defined as above,

A represents optionally halogen-substituted $C_1$–$C_{12}$-alkyl, $C_2$–$C_8$-alkenyl, $C_1$–$C_{10}$-alkoxy-$C_1$–$C_8$-alkyl, represents optionally halogen-, $C_1$–$C_6$-alkyl- or $C_1$–$C_6$-alkoxy-substituted $C_3$–$C_8$-cycloalkyl, in which optionally one or two not directly adjacent methylene groups are replaced by oxygen and/or sulphur or represents optionally halogen-, $C_1$–$C_6$-alkyl-, $C_1$–$C_6$-halogenoalkyl-, $C_1$–$C_6$-alkoxy-, $C_1$–$C_6$- halogenoalkoxy-, cyano- or nitro-substituted phenyl or phenyl-$C_1$–$C_6$-alkyl, B represents $C_1$–$C_{12}$-alkyl or $C_1$–$C_8$-alkoxy-$C_1$–$C_6$-alkyl or A, B and the carbon atom to which they are attached represent $C_5$–$C_{10}$-cycloalkyl or $C_5$–$C_{10}$-cycloalkenyl in which optionally one methylene group is replaced by oxygen or sulphur and which are optionally substituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl or A, B and the carbon to which they are attached represent $C_5$–$C_8$-cycloalkyl or $C_5$–$C_8$-cycloalkenyl in which two carbon atoms are attached to one another by optionally $C_1$–$C_6$-alkyl-, $C_1$–$C_6$-alkoxy- or halogen-substituted $C_3$–$C_6$-alkanediyl, $C_3$–$C_6$-alkenediyl or $C_4$–$C_6$-alkanedienediyl in which optionally one methylene group is replaced by oxygen or sulphur, $R^1$ represents optionally halogen-substituted $C_1$–$C_{20}$-alkyl, $C_1$–$C_{20}$-alkoxy, $C_2$–$C_{20}$-alkenyl, $C_3$–$C_{10}$-alkenyloxy, $C_1$–$C_8$-alkoxy-$C_1$–$C_8$-alkyl, $C_1$–$C_8$-alkylthio-$C_1$–$C_8$-alkyl, optionally $C_1$–$C_6$-alkyl-, $C_1$–$C_6$-alkoxy-, fluorine- or chlorine-substituted cycloalkyl having 3 to 8 ring atoms which may be interrupted by oxygen and/or sulphur atoms, represents optionally halogen-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl or phenoxy;

represents optionally halogen-, $C_1$–$C_6$-alkyl-, $C_1$–$C_6$-alkoxy-, $C_1$–$C_6$-halogenoalkyl-, $C_1$–$C_6$-halogenoalkoxy-substituted phenyl-$C_1$–$C_6$-alkyl or phenyl-$C_1$–$C_4$-alkyloxy, represents optionally halogen- or $C_1$–$C_6$-alkyl-substituted hetaryl, represents optionally halogen- or $C_1$–$C_6$-alkyl-substituted phenoxy-$C_1$–$C_6$-alkyl, represents optionally halogen-, amino- or $C_1$–$C_6$-alkyl-substituted hetaryloxy-$C_1$–$C_6$-alkyl, said process comprising deprotonating with a base a compound of the formula (II)

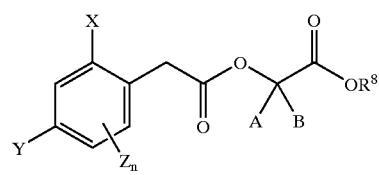

(II)

wherein

X, Y, Z, n, A and B are as defined above and $R^8$ represents $C_1$–$C_6$-alkyl;

reacting the deprotonated compound with a compound of the formula (III)

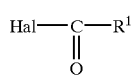

(III)

wherein $R^1$ is as defined above and

Hal represents chlorine or bromine; and collecting the reaction product.

3. A process for preparing a compound of the formula (I)

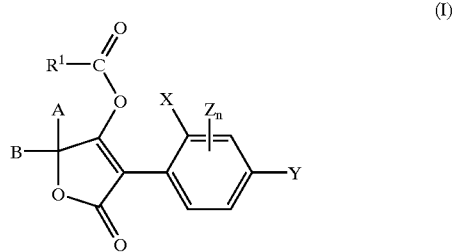

(I)

wherein

X represents $C_1$–$C_4$-alkyl, fluorine, chlorine, bromine, $C_1$–$C_4$-alkoxy or $C_1$–$C_2$-halogenoalkyl, Y represents hydrogen, $C_1$–$C_4$-alkyl, fluorine, chlorine, bromine, $C_1$–$C_4$-alkoxy or $C_1$–$C_2$-halogenoalkyl, Z represents $C_1$–$C_4$-alkyl, fluorine, chlorine, bromine or $C_1$–$C_4$-alkoxy, n represents a number from 0 to 2, A, B and the carbon atom to which they are attached represent $C_5$–$C_8$-cycloalkyl in which optionally one methylene group is replaced by oxygen or sulphur and which is optionally substituted by $C_1$–$C_6$-alkyl, $C_1$–$C_3$-halogenoalkyl, $C_1$–$C_6$-alkoxy, fluorine or chlorine, or A, B and the carbon atom to which they are attached represent $C_5$–$C_6$-cycloalkyl in which two carbon atoms are attached to one another by optionally $C_1$–$C_4$-alkyl-, $C_1$–$C_4$-alkoxy-, fluorine-, chlorine- or bromine-substituted $C_3$–$C_5$-alkanediyl, $C_3$–$C_5$-alkenediyl, in which optionally one methylene group is replaced by oxygen or sulphur, or attached to one another by butadienediyl, $R^1$ represents optionally fluorine- or chlorine-substituted $C_1$–$C_{16}$-alkyl, $C_1$–$C_{16}$-alkoxy, $C_3$–$C_6$-alkenyloxy, $C_2$–$C_{16}$-alkenyl, $C_1$–$C_6$-alkoxy-$C_1$–$C_4$-alkyl, $C_1$–$C_6$-alkylthio-$C_1$–$C_4$-alkyl, optionally methyl-, ethyl-, methoxy-, fluorine- or chlorine-substituted cycloalkyl having 3 to 7 ring atoms which may be interrupted by 1 or 2 oxygen and/or sulphur atoms, represents optionally fluorine-, chlorine-, bromine-, nitro-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl, phenoxy or benzyloxy, represents optionally halogen- or $C_1$–$C_6$-alkyl-substituted hetaryl, said process comprising deprotonating with a base a compound of the formula (II)

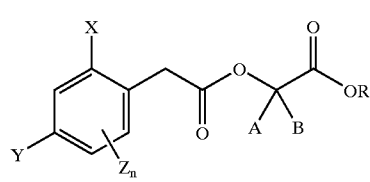

(II)

wherein

X, Y, Z, n, A and B are as defined above and $R^8$ represents $C_1$–$C_4$-alkyl;

reacting the deprotonated compound with a compound of the formula (III)

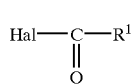

(III)

wherein
R¹ and Hal are as defined above; and
collecting the reaction product.

4. A process for preparing a compound of the formula (I)

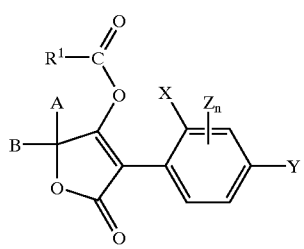

(I)

wherein
X represents methyl, ethyl, propyl, i-propyl, fluorine, chlorine, bromine, methoxy, ethoxy or trifluoromethyl,
Y represents hydrogen, methyl, ethyl, propyl, i-propyl, butyl, i-butyl, tert-butyl, fluorine, chlorine, bromine, methoxy, ethoxy or trifluoromethyl,
Z represents methyl, ethyl, i-propyl, butyl, i-butyl, tert-butyl, fluorine, chlorine, bromine, methoxy or ethoxy,
n represents the number 0 to 1,
A, B and the carbon atom to which they are attached represent $C_3$–$C_8$-cycloalkyl in which optionally one methylene group is replaced by oxygen or sulphur and which is optionally substituted by methyl, ethyl, n-propyl, iso-propyl, trifluoromethyl, methoxy, ethoxy, n-propoxy, iso-propoxy, butoxy or iso-butoxy,
R¹ represents optionally fluorine- or chlorine-substituted $C_1$–$C_{14}$-alkyl, $C_1$–$C_{10}$-alkoxy, $C_2$–$C_{14}$-alkenyl, $C_3$–$C_6$-alkenyloxy, $C_1$–$C_4$-alkoxy-$C_1$–$C_2$-alkyl, $C_1$–$C_4$-alkylthio-$C_1$–$C_2$-alkyl or cycloalkyl having 3 to 6 ring atoms which may be interrupted by 1 or 2 oxygen and/or sulphur atoms,
represents optionally fluorine-, chlorine-, bromine-, methyl-, ethyl-, propyl-, i-propyl-, methoxy-, ethoxy-, trifluoromethyl-, trifluoromethoxy-, nitro-substituted phenyl, phenoxy or benzyloxy;
represents optionally chlorine-, methyl- or ethyl-substituted pyridyl,
said process comprising deprotonating with a base a compound of the formula (II)

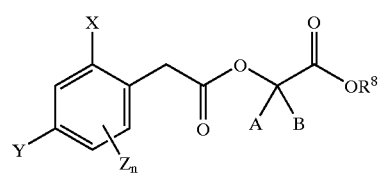

(II)

wherein
X, Y, Z, n, A and B are as defined above and
R⁸ represents methyl, ethyl, propyl or iso-propyl;
reacting the deprotonated compound with a compound of the formula (III)

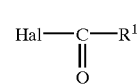

(III)

wherein
R¹ and Hal are as defined above; and
collecting the reaction product.

5. A process for preparing a compound of the formula (Ia)

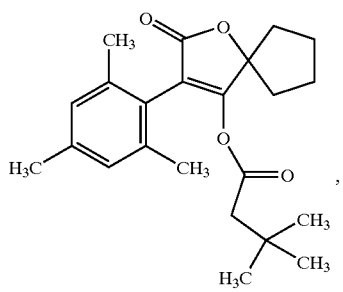

(Ia)

comprising deprotonating with NaOH a compound of the formula (IIa)

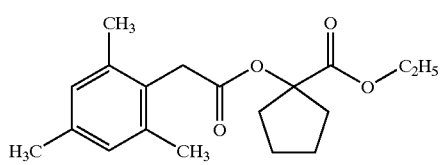

(IIa)

reacting the deprotonated compound with a compound of the formula (IIIa)

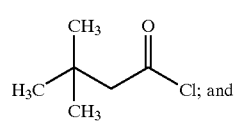

(IIa)

collecting the reaction product.

6. A process for preparing a compound of the formula (Ib)

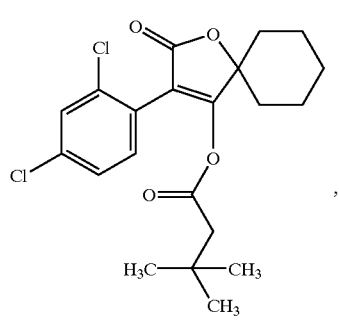

(Ib)

comprising deprotonating with NaOH a compound of the formula (IIb)

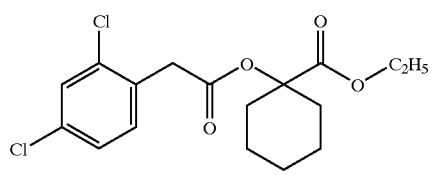 (IIb)
reacting the deprotonated compound with a compound of the formula (IIIb)
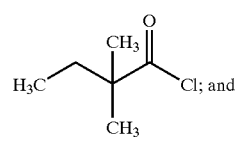 (IIIb)
collecting the reaction product.
* * * * *